(12) United States Patent
Larkin

(10) Patent No.: US 6,571,014 B1
(45) Date of Patent: May 27, 2003

(54) METHOD AND APPARATUS FOR HIGHLY EFFICIENT REPRESENTATION AND COMPRESSION OF IMAGES

(75) Inventor: Kieran Gerard Larkin, Putney (AU)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/295,094

(22) Filed: Apr. 21, 1999

(30) Foreign Application Priority Data

May 7, 1998 (AU) .............................................. PP3406

(51) Int. Cl.[7] .................................................. G06K 9/36
(52) U.S. Cl. ........................ 382/232; 382/125; 382/257
(58) Field of Search ................................ 382/232, 113, 382/115, 116, 125, 124

(56) References Cited

U.S. PATENT DOCUMENTS

| | | | | |
|---|---|---|---|---|
| 4,720,679 A | * | 1/1988 | Patrick et al. ............... | 324/309 |
| 4,833,407 A | * | 5/1989 | Holland et al. .............. | 324/309 |
| 5,027,277 A | * | 6/1991 | Schneider .................... | 701/99 |
| 5,045,950 A | * | 9/1991 | Iwamura et al. ............ | 358/319 |
| 5,144,235 A | * | 9/1992 | Glover et al. ............... | 324/309 |
| 5,204,734 A | * | 4/1993 | Cohen et al. ................ | 356/359 |
| 5,341,099 A | * | 8/1994 | Suzuki ........................ | 324/309 |
| 5,437,281 A | * | 8/1995 | Lin et al. ............... | 128/660.07 |
| 5,543,709 A | * | 8/1996 | Kajiyama .................... | 324/309 |
| 5,588,026 A | * | 12/1996 | Ishikawa et al. ............ | 375/329 |
| 5,659,626 A | | 8/1997 | Ort et al. ..................... | 382/125 |
| 5,680,485 A | | 10/1997 | Loce et al. .................. | 382/257 |
| 5,748,783 A | | 5/1998 | Rhoads ........................ | 382/232 |
| 5,799,098 A | | 8/1998 | Ort et al. ..................... | 382/125 |
| 5,920,641 A | | 7/1999 | Ueberreiter et al. ........ | 382/125 |
| 5,995,551 A | * | 11/1999 | McCallister et al. ........ | 375/265 |
| 6,043,870 A | * | 3/2000 | Chen ........................... | 356/35.5 |
| 6,066,949 A | * | 5/2000 | Alley et al. .................. | 324/309 |

FOREIGN PATENT DOCUMENTS

| | | | |
|---|---|---|---|
| DE | 41 10 951 A | 10/1992 | .......... H04N/13/00 |
| WO | 96/07976 | 3/1996 | |

OTHER PUBLICATIONS

Mallat et al., "Singularity Detection and Processing with Wavelets", IEEE Transactions on Information Theory, vol. 38, No. 2, Mar. 1992, pp. 617–643.*

Mallat et al., "Singularities and Noise Discrimination with Wavelets", IEEE International Conference on Acoustics, Speech, and Signal Processing, vol. 4, 1992, pp. 377–380.*

(List continued on next page.)

*Primary Examiner*—Anh Hong Do
(74) *Attorney, Agent, or Firm*—Fitzpatrick, Cella, Harper & Scinto

(57) ABSTRACT

A method of encoding images such as fingerprint type images (FIG. 2) is disclosed. A phase map structure for the image is formed (FIG. 3) and any singularities (+1, 2, 0.5) in the phase map structure are removed to create a continuous phase map structure (FIG. 5). The structure of the singularities and the continuous phase map structure are then separately encoded to form an encoded representation (88) of the image (50). Preferably, the singularity encoding includes encoding a position of each singularity in addition to its order and orientation. The phase map structure can be of the form:

$$f(x,y)=a(x,y)+b(x,y)\cos(\phi(x,y))+c(x,y)+n(x,y)$$

The significance map can further include a separate encoding of phase map magnitude components.

49 Claims, 6 Drawing Sheets

OTHER PUBLICATIONS

Bradley J. N. et al., "The FBI Wavelet/Scalar Quantization Standard For Gray–Scale Fingerprint Image Compression", Proceedings of the SPIE, Bellingham, VA, US, No. 1961, Apr. 1993, pp. 293–304, XP001060246.

Hopper, "Compression of gray–scale fingerprint images", SPIE, vol. 2242 Wavelet Applications, pp. 180–187, 1994.

Kujawinska, "Spatial Phase Measurement Methods", Interferogram Analysis, Digital Fringe Pattern Measurement Techniques, 1993, pp. 141–193.

Larkin, "Efficient Nonlinear Algorithm for Envelope Detection in White Light Interferometry" J. Opt. Soc. Am. A, vol. 13, No. 4, 4/96, pp/ 832–843.

Stetson et al., "Noise Immune Phase Unwrapping by Use of Calculated Wrap Regions", Applied Optics, vol. 36, No. 20, Jul. 10, 1997, pp. 4830–4839.

W.M. Telford et al., Applied Geophysics, pp. 385–400.

* cited by examiner

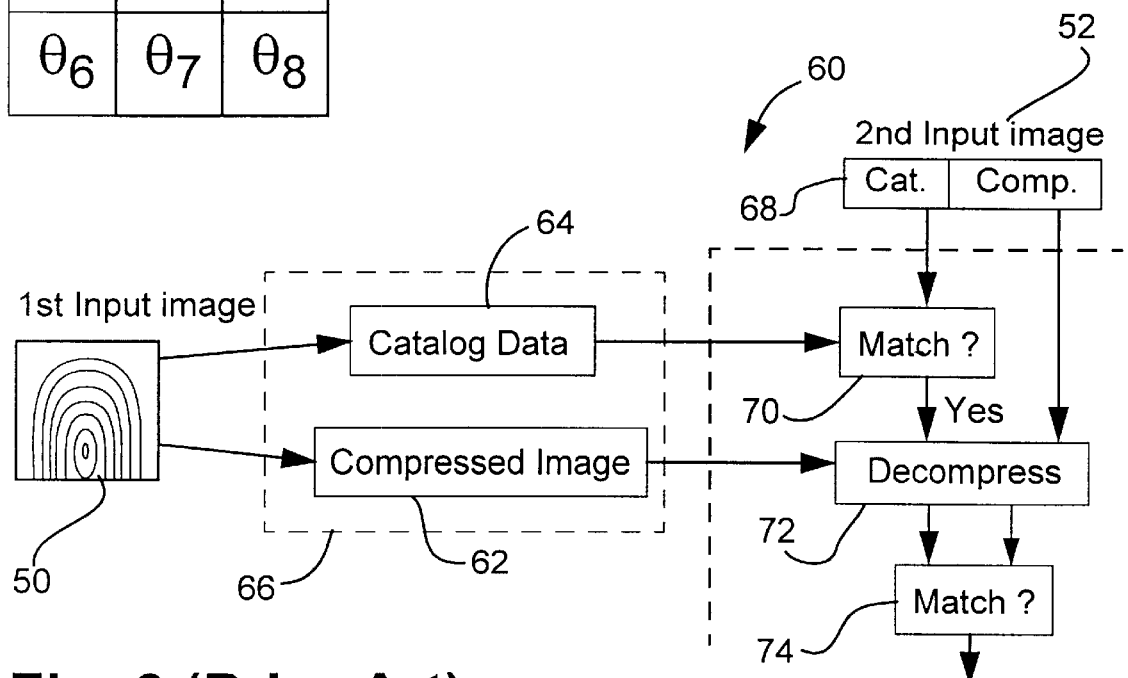
Fig. 4
Fig. 6 (Prior Art)
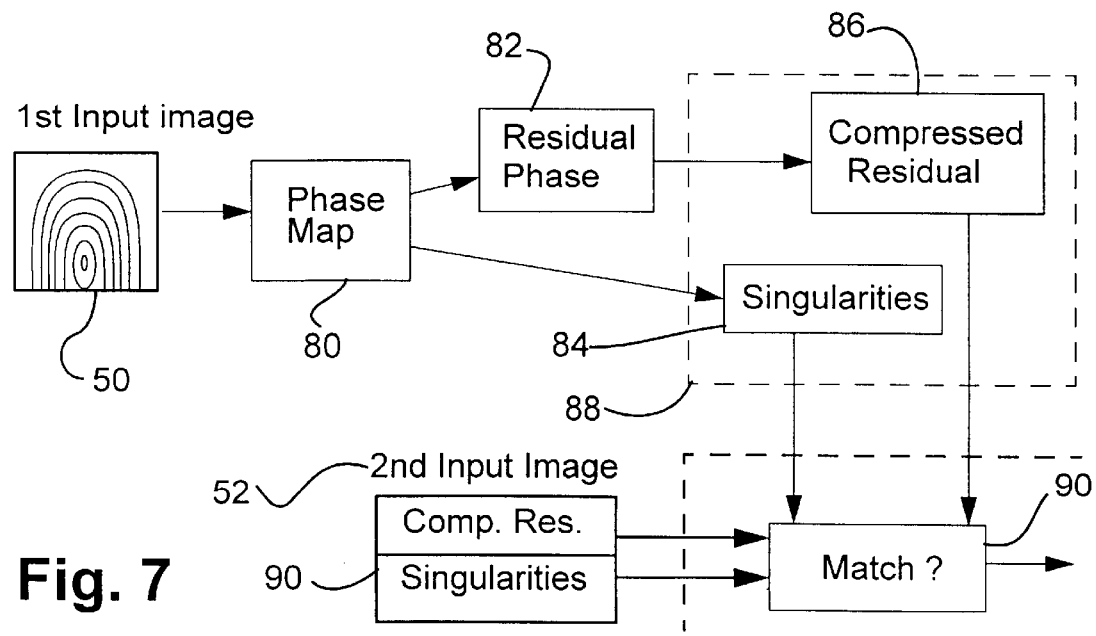
Fig. 7

METHOD AND APPARATUS FOR HIGHLY EFFICIENT REPRESENTATION AND COMPRESSION OF IMAGES

FIELD OF THE INVENTION

The present invention relates to the digital compression of images and, in particular, to an efficient method of representing the essence of an image as a phase modulated structure. The present invention finds application in the coding of a variety of images, and is of particular relevance to the representation of "fingerprint" type images.

BACKGROUND ART

The compression of grey-scale fingerprint images is an important problem in the field of digital image compression. In one recent proposal utilised by the United States Federal Bureau of Investigation (FBI), an algorithm based on a scalar quantisation of a discrete wavelet transform decomposition of the image, followed by run length encoding and Huffman encoding has been implemented. For an example of discussion of the technique utilised, see "Compression of Gray-Scale Fingerprint Images" by Tom Hopper appearing in SPIE Vol. 2242, entitled Wavelet Applications (1994) at pp 180–187. The reported compression factors for the wavelet based compression were typically 15:1, and at best about 20:1.

Fingerprint ridges are not necessarily continuous across an impression but suffer interruptions such as ridge endings or bifurcations. Collectively, these interruptions are known as minutiae. The definitive information utilised to determine whether one fingerprint matches another is the fine detail in these ridges—the minutiae and their relationships. Hence, it is normally considered important that for fingerprint compression applications that the fidelity of the ridge detail is retained in the compression and decompression transformations.

The process of fingerprint identification (matching) and fingerprint image compression are based on two unrelated methods. The typical compression scheme utilised is wavelet compression. The wavelet compression schemes are essentially general image compression schemes and do not take advantage of the particular structure of a fingerprint image. The matching schemes characterise the minutiae by type, orientation and position. These features are then catalogued and stored as essentially separate data to the compressed image. Automatic fingerprint identification is achieved by comparing a list of the catalogued features with a data base of stored lists. When a match is detected, the "matching" fingerprint is decompressed for direct comparison with the fingerprint in question.

Whilst such an arrangement affords fast high-level matching, the fine detail that characterises the minutiae is not considered until the more time consuming direct comparison. Significantly, although the catalogued features may be thought of as compressed data, such does not represent the compressed image and it is desirable for matching to be based on the image, rather than some catalogued summary thereof. It is thus desirable to provide for a system that provides for high compression ratios whilst permitting the automatic classification of minutiae, thus promoting automatic matching systems.

SUMMARY OF THE INVENTION

In accordance with a first aspect of the present invention, there is provided a method of encoding an image, the method comprising the steps of determining a phase map structure for the image; and encoding the phase map structure.

In accordance with a second aspect of the present invention, there is provided a method of encoding an image, the method comprising the steps of determining a phase map structure for the image; removing any singularities in the phase map structure to create a continuous phase map structure; and separately encoding the singularities and the continuous phase map structure as an encoded representation of the image.

Preferably, the singularity encoding includes encoding a position of each singularity in addition to its order and orientation. The phase map structure can be of the form:

$$f(x,y)=a(x,y)+b(x,y)\cos(\phi(x,y))+c(x,y)+n(x,y)$$

The magnitude of the phase modulated component can be separately encoded as what is termed herein a "significance map". The significance map represents the relative importance of all phase components. Advantageously the image is a fingerprint-type image.

BRIEF DESCRIPTION OF THE DRAWINGS

Notwithstanding any other forms which may fall within the scope of the present invention, preferred forms of the invention will now be described, by way of example only, with reference to the accompanying drawings in which:

FIG. 4 illustrates the process of locating discontinuities in the phase map;

FIG. 6 depicts a prior art compression and matching scheme;

FIG. 7 depicts a compression and matching scheme according to the preferred embodiment.

DETAILED DESCRIPTION

Figure 1:
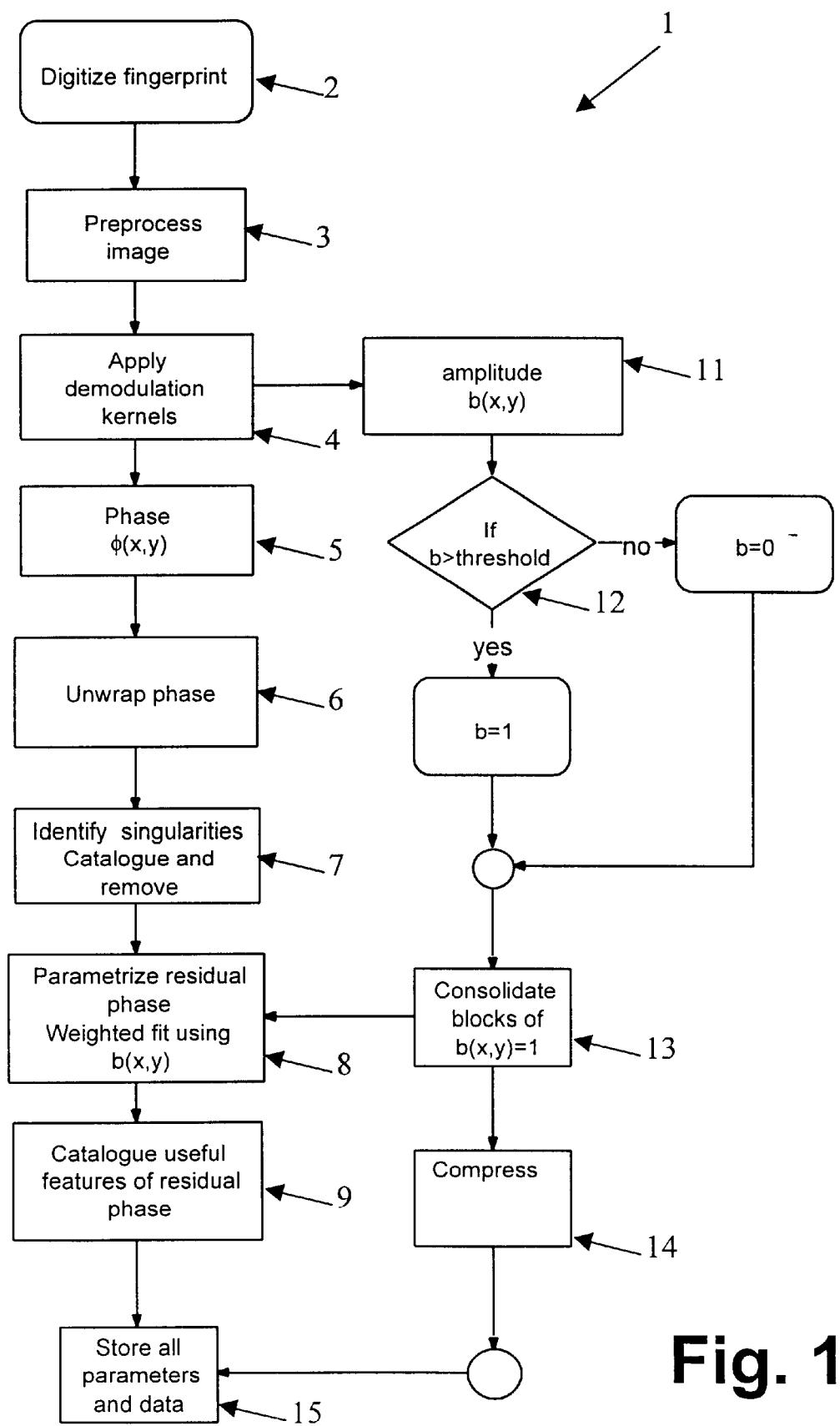
FIG. 1 illustrates a flow chart of the steps of the preferred embodiment.

The preferred embodiment can be understood through a number of important initial observations in respect of fingerprint images, those being:

Fingerprints generally consist of a series of nearly equally spaced ridges and valleys. This structure is believed to be related to the reaction-diffusion dynamics occurring at morphogensis; and Fingerprints resemble optical interference patterns (fringe patterns).

Important features of fingerprints often correspond to dislocations in the fringe patterns (for example: bifurcations of fringes, fringe endings, spirals or whorls).

The preferred embodiment involves harnessing these various observations in the production of an efficient compression system. The present inventor has determined that fingerprint images and their minutiae can be compactly represented by an equation of the form:

$$f(x,y)=a(x,y)+b(x,y)\cos(\phi(x,y))+c(x,y)+n(x,y) \quad \text{Equation (1)}$$

In Equation (1), $f(x,y)$ represents the intensity of the fingerprint image and includes four main terms. Position coordinates (x,y) within the image may be continuous for an analog image and discrete for digital images. A slowly varying background level is denoted by $a(x,y)$ while the amplitude modulation term is $b(x,y)$. Perhaps the most important term is $\phi(x,y)$ which represents the phase of the "fringe" pattern associated with the fingerprint. Real fingerprints need an additional term to represent them accurately. This term may be called noise $n(x,y)$ because it contributes little useful information to the image, and contains such features as blurring, harmonics, smudging, scratches, cuts and dust. Finally, there is a term $c(x,y)$ to represent additional features (such as pores) that are potentially significant features, but cannot be can be contained in the first two terms.

An idealised fingerprint (without pores and defects) can be represented in a simplified form by the first two terms in equation (1) with: a≡b≡1, ie.:

$$f(x,y)=1+\cos(\phi(x,y)) \quad \text{Equation (2)}$$

In this situation, all the useful information regarding the fingerprint is contained in the phase function $\phi(x,y)$. Although $f(x,y)$ is (generally) a rapidly varying function of (x,y), the phase $\phi(x,y)$ is (generally) a slowly varying function of (x,y). This factor can therefore be used in the compression process. If $f(x,y)$ can be (accurately) demodulated to reveal the phase $\phi(x,y)$, then high compression ratios are attainable for the slowly varying $\phi(x,y)$ and therefore for $f(x,y)$, which can be reconstructed (or decompressed/decoded) using Equation (2).

It should be noted $\phi(x,y)$ is only a slowly varying function if it has been "unwrapped" correctly, and the phase singularities identified and removed. Assuming it is possible to extract the phase, characterise and remove any phase singularities, and correctly unwrap the residual phase (a process which will be described hereinafter), then it is possible to:

compress the residual phase using conventional (eg. wavelet) compression techniques or parametrically compress using 2D polynomial or spline fitting; and catalogue the phase singularities which correspond directly to the so called minutiae of conventional fingerprint analysis. This catalogue has entries with just 4 parameters for each singularity.
1. singularity x location
2. singularity y location
3. singularity "charge" or order
4. singularity phase (or orientation).

The catalogue is an integral part of the compression data, but also contains the data for a matching process. At this point it should be mentioned that the residual phase is also useful for matching as it contains such information as the number of ridges (and their orientation) between minutiae. The information will be apparent in the residual phase and does not need to be decompressed to obtain this data if the local residual phase is noted and catalogued at each singularity location. This allows matching to be performed in the compressed domain if desired. Such matching may be performed using the singularities and the singularity locations within the residual phase without the need to decompress the residual phase.

Turning now to FIG. 1 there is shown in more detail the main steps of a method 1 in accordance with the preferred embodiment. The steps are now described in detail.

The method 1 starts with the digitizing 2 of an image, such as that of a fingerprint. This may include a scan from a fully automatic fingerprint imaging system, or a system for digitising ink on paper prints. The method may also use latent fingerprints which have been developed using forensic techniques. Present optically based fingerprinting devices, however, give much higher quality images with which the method 1 may commence.

A preprocessing stage 3 follows the digitizing step 2 and is utilised to remove gross image defects such as smearing or over-inking. The amount of preprocessing performed is dependent upon the input data source and some amount of preprocessing is likely with most input images. However, for the purposes of discussion of the preferred embodiment, a relatively high quality image from an optical input device is assumed.

A demodulation stage 4 follows to extract at least a phase component of the image. Demodulation preferably uses compact kernel algorithms for spatial carrier demodulation methods such as those disclosed in M. Kujawinska, "Spatial Phase Measurement Methods" in Interferogram Analysis: Digital Fringe Pattern Measurement Techniques, D. W. Robinson and G. T. Reid, eds (Institute of Physics, Bristol, U.K. 1993). There are many algorithms which could be used, both 1-dimensional and 2-dimensional. In principle, methods such as the Fourier (Hilbert) Transform Method may also be used.

In the preferred embodiment a simple 2D adaptive demodulator is chosen, but other algorithm may be chosen to suit the characteristics of the data. The 1D version of this demodulator is derived and explained in, for an example, "Efficient Nonlinear Algorithm for Envelope Detection in White Light Interferometry", Larkin, K. G.; *J. Opt. Soc. Am. A*/Vol. B, No. 4, April 1996, pp 832–843.

Consider the basic fringe pattern structure of the fingerprint:

$$f_h(x,y)=a(x,y)+b(x,y)\cos(\phi(x,y)) \quad \text{Equation (3)}$$

The observation that the fringe spacing is near-constant can be written mathematically as the phase derivative (or frequency) having two components, one of which has a constant magnitude σ, i.e.

$$\phi(x,y)=2\pi(ux+vy)+\psi \quad \text{Equation (4)}$$

and $$u^2+v^2=\sigma^2 \quad \text{Equation (5)}$$

The nominal orientation of the fringe is defined by the angle β, where:

$$\tan\beta = \frac{v}{u} \quad \text{Equation (6)}$$

Figure 2:
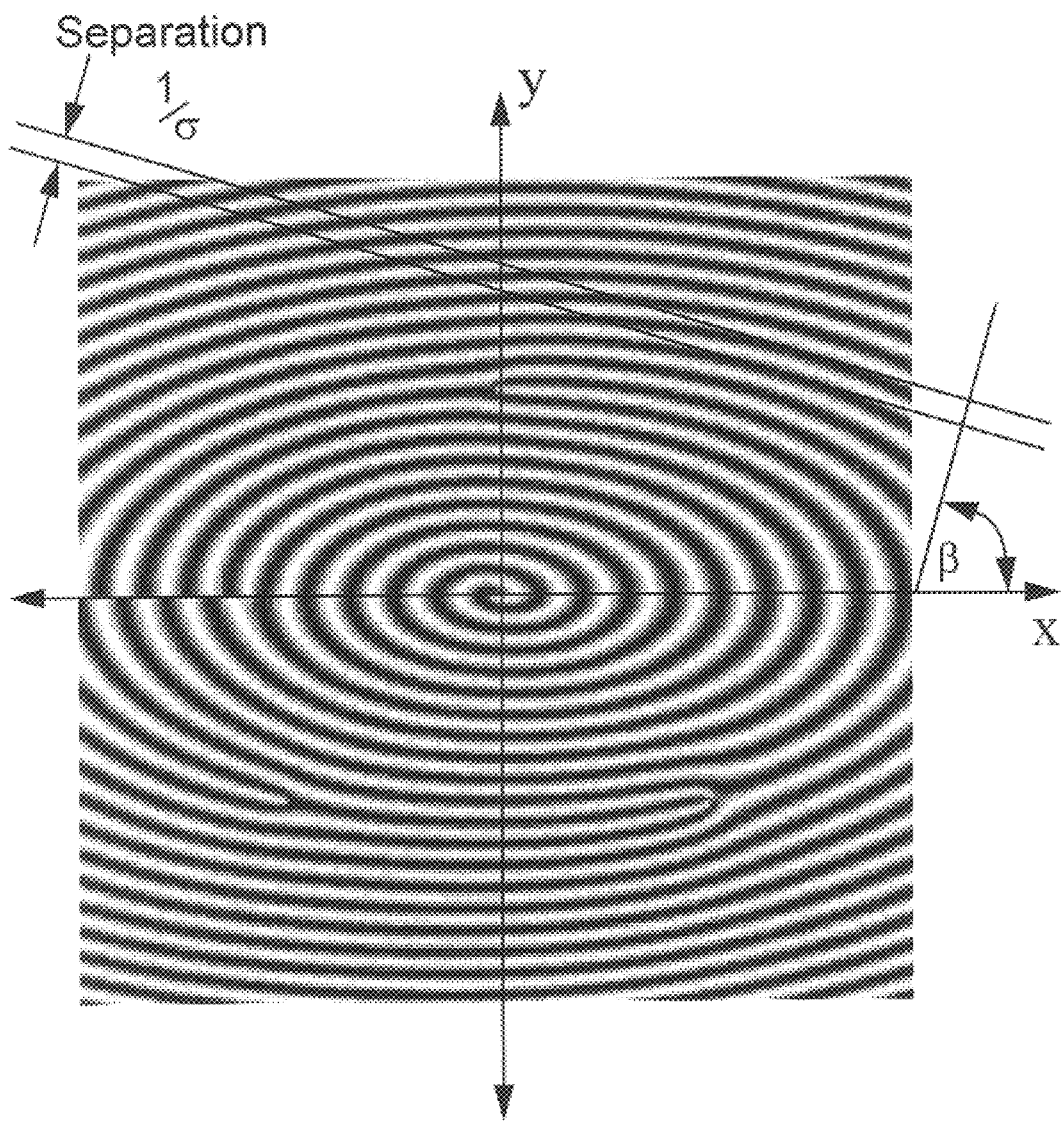
FIG. 2 illustrates an example synthetically created "fingerprint"

A typical case of a simulated fingerprint image illustrating the angle orientation β of the fringe is illustrated in FIG. 2.

As seen in FIG. 2, the separation between fringes 1/σ and the angle β (normal to the fringes) provide two values that may be utilized for fingerprint analysis. Significantly the present inventor has realised that the information implicit in the combination of these two values may be encapsulated in a single representation based on the phase φ of the fringe pattern.

The objective of the demodulation step 4 is to recover the phase φ from the fringe pattern $f$. Conventional spatial carrier phase-shifting algorithms can demodulate the phase over a small range of frequencies (phase derivative). However, a fingerprint pattern represents a fringe structure which has x and y components of frequency which vary over a wide range. A useable demodulation algorithm must adapt to the local fringe pattern.

A convenient approach may be based upon a five sample non-linear phase-shifting algorithm. Consider five successive samples of the digitised fingerprint:

$$I_{-2}=f_b(x-2,y)$$
$$I_{-1}=f_b(x-1,y)$$
$$I_0=f_b(x,y) \quad \quad \text{Equation (7)}$$
$$I_{+1}=f_b(x+1,y)$$
$$I_{+2}=f_b(x+2,y)$$

From this base data it is possible to construct symmetrically filtered components as follows:

$$c_1=-I_{-1}+2I_0-I_{+1}$$
$$c_2=-I_{-2}+2I_0-I_{+2} \quad \quad \text{Equation (8)}$$
$$s_1=-I_{-1}+I_{+1}$$
$$s_2=-I_{-2}+I_{+2}$$

From this, and according to step 5 of FIG. 1, it is possible to extract the phase, modulation and frequency parameters. One particular form is a robust estimator (which avoids the conventional problem of zero-by-zero division), for fringe patterns with between 3 and 8+ pixels per fringe:

$$\alpha = 2 \arccos\left\{ \frac{1}{2} \sqrt[4]{\frac{(2s_1+s_2)^2+c_2^2}{s_1^2+c_1^2}} \right\} \quad \text{Equation (9)}$$

Thus, the actual phase may be recovered in a number of ways. One method integrates α with respect to x to get φ. In general, this can be combined with a corresponding y integration to get all components of φ. An alternative is to substitute (9) back into (3) and (7) to get:

$$b\sin(\phi) = -\frac{\text{sgn}(s_1)}{4\sin(\alpha)}\sqrt{\frac{s_2^2+4s_1^2}{1+\cos^2(\alpha)}} \quad \text{Equation (10)}$$

$$b\cos(\phi) = \frac{c_2+4c_1}{16\sin^2(\alpha/2)[1+\cos^2(\alpha/2)]} \quad \text{Equation (11)}$$

and $$\tan(\phi) = \frac{b\sin(\phi)}{b\cos(\phi)}. \quad \text{Equation (12)}$$

There are certain advantages to initially calculating the phase derivatives with respect to x and y. Primarily, the next step 6 of FIG. 1, of unwrapping the phase, is simplified by the use of phase derivatives. Unwrapping the phase involves removing 2π phase discontinuities due to the modulo 2π character of the inverse trigonometric functions used to calculate φ in Equation (12) for example. The phase calculated from Equation (12) can have ambiguities owing to an assumption about the orientation of the fringes. This means that the sign of the numerator of Equation (12) does not always change as required as the orientation angle β is moved in the range zero to 2π radians. Consequently the phase output from Equation (12) can have regions of π radian wrapping. This ambiguity can be resolved in several ways. One way is to consider continuity of phase over regions and negate the numerator as required to reduce the overall discontinuities. An alternative method is to negate the numerator in a systematic manner to formally minimize the "global" (summed over the entire image) number of discontinuities. A global minimum in the discontinuities also ensures a well defined solution with maximum compressibility of the final residual phase map. In both cases the output is a 2π radian wrapped phase map derived from a π radian wrapped phase map. There are numerous schemes for unwrapping the 2π radian phase maps. For example, see "Noise Immune Phase Unwrapping by Use of Calculated Wrap Regions", Stetson et al, *Applied Optics* Vol. 36, No. 20, Jul. 10, 1997 pp 4830–4839. The phase demodulated and unwrapped version of the image of FIG. 2 is shown in FIG. 3.

Figure 3:
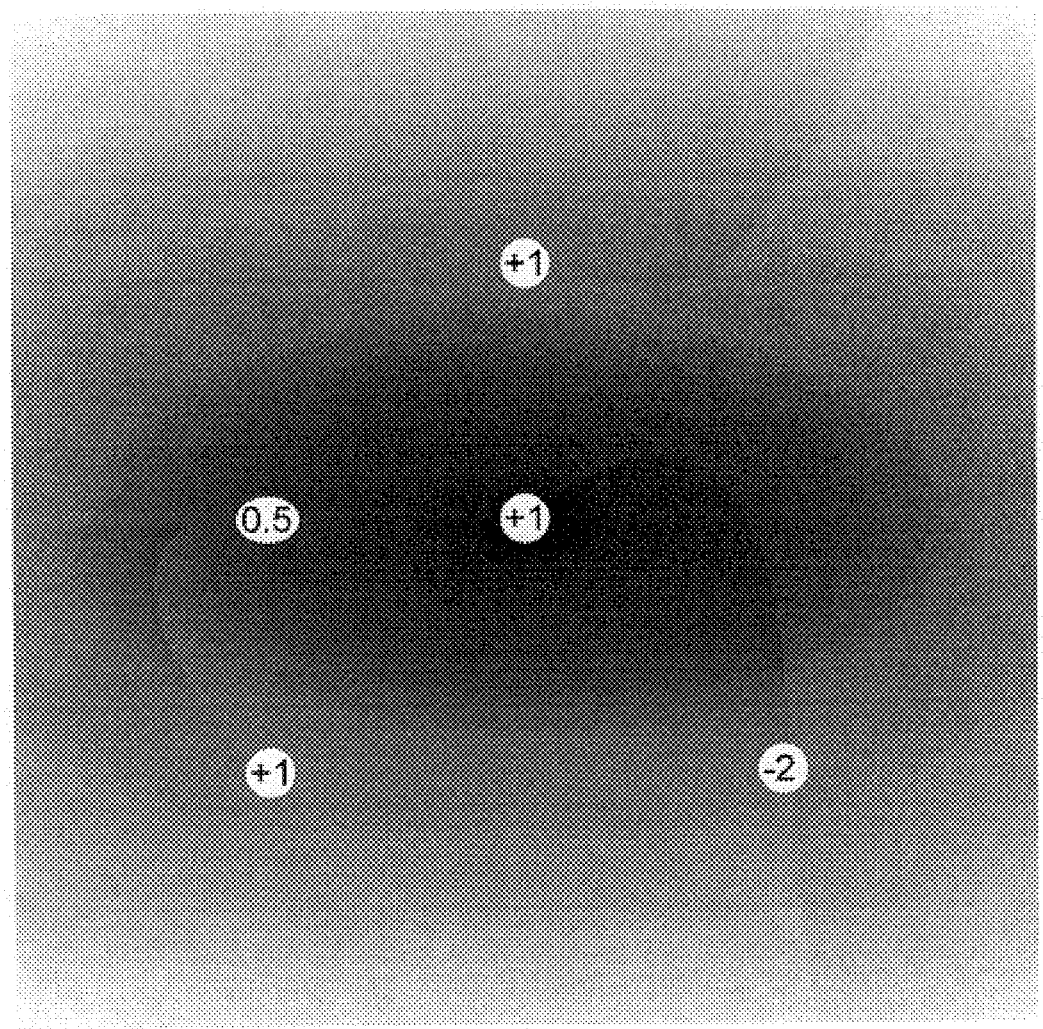
FIG. 3 illustrates a phase map of the "fingerprint" of FIG. 2.

The phase singularities (or dislocations) are identified in FIG. 3 by white circles containing the value of the spiral phase "charge". A spiral phase of charge (or order) +C, located at $(x_0,y_0)$ can be represented mathematically by h(x,y), where the modulo 2π arctangent function is used as follows:

$$h(x,y)=C.\arctan(y-y_0,x-x_0). \quad \text{Equation (13)}$$

The charge is usually an integer, positive or negative, and represents the number of 2π phase shifts which occur in one polar rotation. The example shown in FIG. 3 actually contains a one half order discontinuity (C=0.5) which has a characteristic misalignment, or shear, of the fringes. Integer order charges do not exhibit this shearing effect but do have the effect of bifurcating or terminating fringes, this being best seen in FIG. 2. A charge of ±1 introduces a bifurcation. A charge of ±2 introduces tri-furcation, and so on. The presence of a phase spiral is readily detected in a locality by choosing any closed path and summing the phase differences (each modulo 2π) as the loop is traced. Any region containing just one singularity will have a total equalling 2π times the charge. Regions with no singularities have zero total charge. Regions with more than one singularity give a total equal to the total charge. This means that positive and negative charges cancel for loops containing both singularities.

Having unwrapped the phase at step 6, the detection of singularities can now be performed at step 7.

The essential details of a preferred singularity detection scheme are described below, but any method which detects phase spirals may be substituted. The simplest detector uses just 3×3 pixels in a typical convolution kernel. The central value is ignored and the 8 surrounding pixels are used to estimate the spiral phase component. Working around these 8 pixels counter-clockwise, the phase increments from pixel to pixel are calculated modulo 2π. FIG. 4 shows a suitable 3×3 kernel arrangement. To avoid unintentional or additional wraparound, the following relation can be used:

$$\Delta_{n+1} = \text{mod}_{2\pi}(\theta_{n+1}-\theta_n) = \arctan\left(\frac{\sin\theta_{n+1}\cos\theta_n - \sin\theta_n\cos\theta_{n+1}}{\cos\theta_{n+1}\cos\theta_n + \sin\theta_n\sin\theta_{n+1}}\right) \quad \text{Equation (14)}$$

From this expression the total of the 8 phase increments is found. To calculate the first increment (n=0) the pixel order is wrapped and the pixel n=8 is used to represent n=0. The total is used to estimate the presence and strength of any spiral phase. For example, a charge +1 spiral will have a total of $2\pi$ if the system is noise free. The procedure can be repeated for larger loops (e.g. the outside loop of the 5×5 or 7×7 kernel) to reduce noise sensitivity.

Once all the singularities have been identified with a predefined confidence level, they can be characterised and catalogued as outlined earlier in the following manner:

1. singularity x location
2. singularity y location
3. singularity "charge" or order
4. singularity offset (or orientation).

Once this is accomplished, the pure singularities can be subtracted from the phase, leaving a residual phase map with no singularities. The singularity removal may proceed as follows. Assuming a singularity of charge +1 has been detected at position $(x_0,y_0)$, then it is possible to add a phase spiral of opposite charge:

$$-\arctan(y-y_0, x-x_0). \qquad \text{Equation (15)}$$

This has the effect of cancelling (or removing) the effect of the phase singularity over the entire phase map. This contrasts prior art methods which have been local in their processing and which, having acknowledged the existence of singularities, have been unable to practically deal with them. The present inventor has determined that global removal is a way to remove singularities without introducing nearby (local) artefacts and errors.

Alternatively, and advantageously, steps 6 and 7 of FIG. 1 may be swapped in their execution, this providing singularity detection and removal before $2\pi$ phase unwrapping is performed. This simplifies and accelerates the unwrapping process.

The remaining phase map is characterised by a gradient of almost constant magnitude, this being a mathematical way of saying that the original fingerprint was characterised by ridges and valleys of almost constant pitch or separation. A consequence of this is that the residual phase map may be well represented by a simple (smooth) polynomial or spline type function. The function may be found, using a least square fit process for example, and the residual phase map can be represented by a function with a small number of parameters as depicted in step 8 of FIG. 1. These parameters, in fact, constitute the compressed, or encoded residual phase map.

Figure 5:
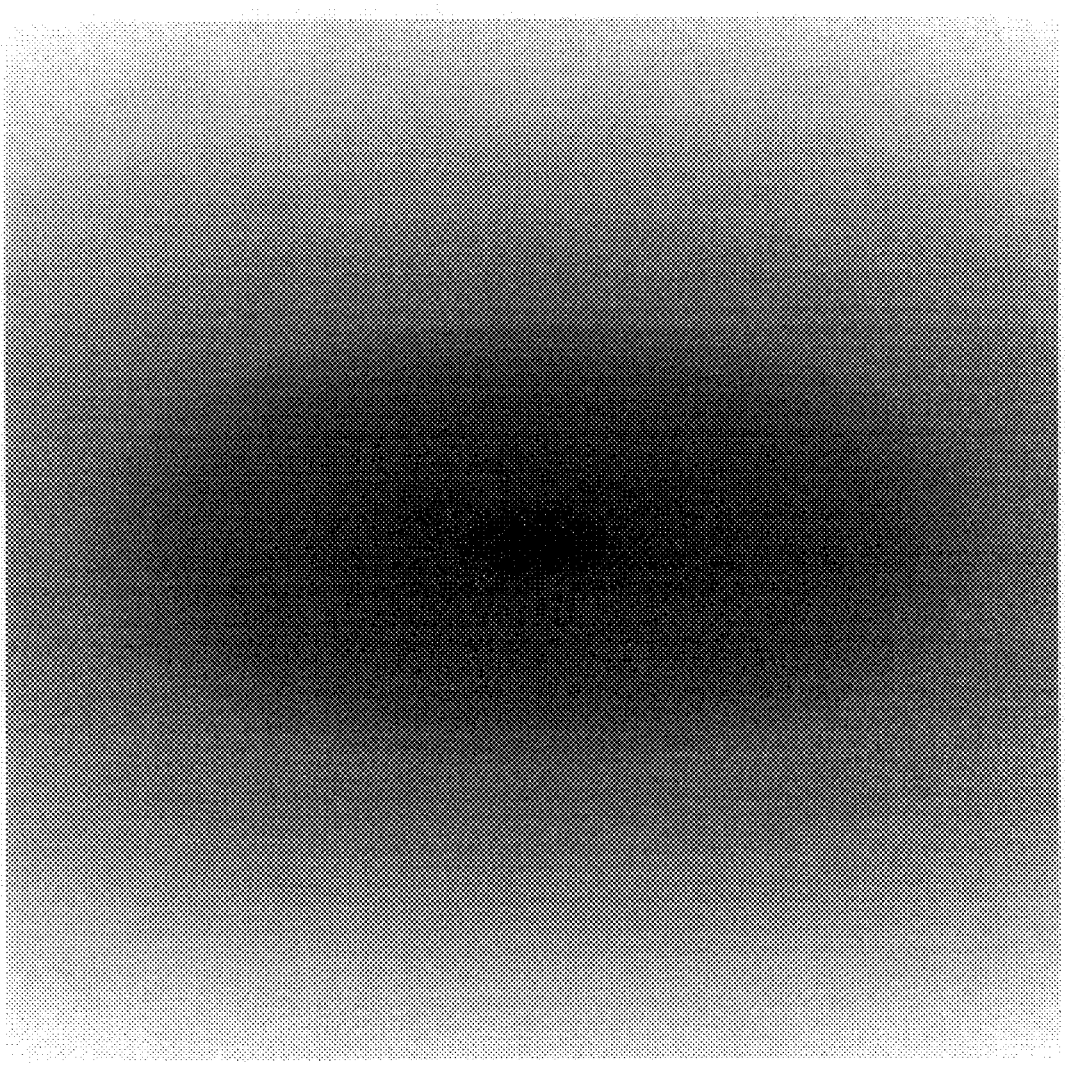
FIG. 5 illustrates the resultant phase map after removal of the singularities.

FIG. 5 shows an example of the residual phase map derived from the fingerprint of FIG. 2, which is seen to be almost devoid of information, other than an (almost constant) change in shading from the centre to the extremities. As a consequence, in this particular case, the residual phase map can be represented by (compressed to) less than half a dozen floating point numbers. A more robust method of compression at this point may be to use wavelet compression for the residual phase map. Because the singularities have been removed (which compress very poorly with wavelets), the residual phase allows very high compression ratios combined with high quality, due to the near constant gradient detailed earlier. In combination with the singularity characteristics calculated earlier, these form the compressed data-set. Significantly, the combination of the singularities and the residual phase at each singularity location provide a basis by which matching may be performed on a compressed data structure according to the preferred embodiment.

As seen in step 9 of FIG. 1, the location and separation of spiral singularities may be catalogued in pixels, or, more meaningfully as a phase, in multiples of $2\pi$ radians. The second method is more robust to distortions because it is inherently an invariant of the fingerprint. Further, the latter actually corresponds to the number of ridge/valley pairs between singularities.

It should be noted that real fingerprints will have regions of very low (or zero) modulation. This information is implicit in the amplitude variable b(x,y) of Equation 3. FIG. 1 also shows one method of a demodulation scheme that calculates and processes b(x,y). The utilisation of the variable b(x,y) determines whether or not image regions are useable or not. Firstly, the demodulation kernel process 4 can also output an amplitude component 11 at each X and Y position. A test 12 is conducted to determine if the amplitude is significant and those blocks determined to be significant 13 are utilised in the parameterisation process 8. The significance map can also be separately compressed 14 (for example, by run length encoding) and stored 15 with the other phase data.

The foregoing schema provides for high levels of compression of fingerprint type images. With the artificial fingerprint of FIG. 2, the preferred embodiment can provide for a compression ratio of 1000:1 or better. However, for real fingerprints, because of the presence of discontinuities caused by dirt, skin damage and the like, compression ratios typically better than 100:1 are expected. Further, the compression scheme utilised leads naturally to a system for matching minutiae as the compressed data is naturally divided into a phase map and the singularities which are precisely the singularities of significance. Hence, in the matching process it is not necessary to decompress the data.

FIG. 6 shows a prior art fingerprint storage and matching system 60 where a first input image 50 is desired to be stored as part of a database for subsequent matching with other fingerprint images such as a second input image 52. In this prior art arrangement, the input image is compressed to give compressed image data 62. Also, catalogue data 64 as discussed previously is derived, either manually or through automatic means. Together, the catalogue data 64 and the compressed image data 62 form an individual record 66 that may be stored in a database (not illustrated). When a matching or comparison process is desired, a corresponding data record 68 of the second input image 52 is extracted. Initially, the catalogue data of each record are compared in a match detector 70. Where a match occurs, each of the corresponding compressed images are decompressed 72 and a match detection 74 applied between the actual images 50 and 52. The match detection 74 is typically manually performed although recently automated methods have been developed to reduce the amount of manual comparison required.

FIG. 7 shows how the encoding method of the preferred embodiment can be used to simplify the matching process. As seen, the first input image is processed to form a phase map 80 including a residual phase component 82 and singularities 84. The residual phase component 82 is compressed (encoded) by an appropriate process to give a compressed residual 86. The singularities 84 and compressed residual 86 together form a single (compressed) record 88 of the image 50 that may be stored in a database. When it is desired to match the first image 50 with a second image 52, having a corresponding compressed record 90, each of the records 88 and 90 may be input to a matching process 92 which operates on the combination of the singularity information and the residual phase at the singularity location of each record 88,90 to perform matching without a need to decompress either or both of the records 88,90.

Through performing matching based upon the records 88,90, the matching process can be greatly accelerated compared to the arrangement of FIG. 6. This is due to the match 90 being more accurately performed on the compress data set 88 than that performed on the prior art data set 66. Once a match is identified each of the records 88,90 may be decompressed to allow for manual confirmation of the match if desired.

Decompression of the records 88, 90 may be performed by reversing the encoding process. Specifically, the encoded residual phase is decompressed using the complement of it's encoding process, to which is added the singularities obtained directly from the corresponding record 88, 90, to provide the original phase map structure. The phase is then combined with the amplitude components and inverse transformed back to Cartesian coordinates having a displayable amplitude, thus representing the original image, which may then be displayed. Optimally, the phase is combined with a "smoothed" version of the amplitude components, obtained by removing noise and artefact components c(x,y) and n(x,y).

The preferred embodiment of the present invention incorporating the method 1 and the above noted equations may be implemented as a computer application program hosted by an operating system forming part of a general purpose computer system. The application program has a user interface which includes menu items and controls that respond to mouse and keyboard operations. The application program has the ability to transmit data to one or more printers either directly connected to a host computer or accessed over a network. The application program also has the ability to transmit and receive data to a connected digital communications network (for example the "Internet").

The preferred embodiment of the invention can be practised using a conventional general-purpose (host) computer system, such as the computer system 100 shown in FIG. 8, wherein the application program discussed above and to be described with reference to the other drawings is implemented as software executed on the computer system 100. The computer system 100 comprises a computer module 101, input devices such as a keyboard 102 and mouse 103, output devices including a printer 115 and a display device 114. A Modulator-Demodulator (Modem) transceiver device 116 is used by the computer module 101 for communicating to and from a communications network 120, for example connectable via a telephone line or other functional medium. The modem 116 can be used to obtain access to the Internet, and other network systems.

The computer module 101 typically includes at least one processor unit 105, a memory unit 106, for example formed from semiconductor random access memory (RAM) and read only memory (ROM), input/output (I/O) interfaces including a video interface 107, and an I/O interface 113 for the keyboard 102 and mouse 103 and optionally a joystick (not illustrated), and an interface 108 for the modem 116. A storage device 109 is provided and typically includes a hard disk drive 110 and a floppy disk drive 111. A CD-ROM drive 112 is typically provided as a non-volatile source of data. The components 105 to 113 of the computer module 101, typically communicate via an interconnected bus 104 and in a manner which results in a conventional mode of operation of the computer system 100 known to those in the relevant art. Examples of computers on which the embodiments can be practised include IBM-PC's and compatibles, Sun Sparcstations or alike computer systems evolved therefrom. Typically, the application program of the preferred embodiment is resident on the hard disk drive 110 and read and controlled in its execution by the processor 105. Intermediate storage of the program and any data fetched from the network 120 may be accomplished using the semiconductor memory 106, possibly in concert with the hard disk drive 110. In some instances, the application program may be supplied to the user encoded on a CD-ROM or floppy disk, or alternatively could be read by the user from the network via the modem device 116.

Figure 8:
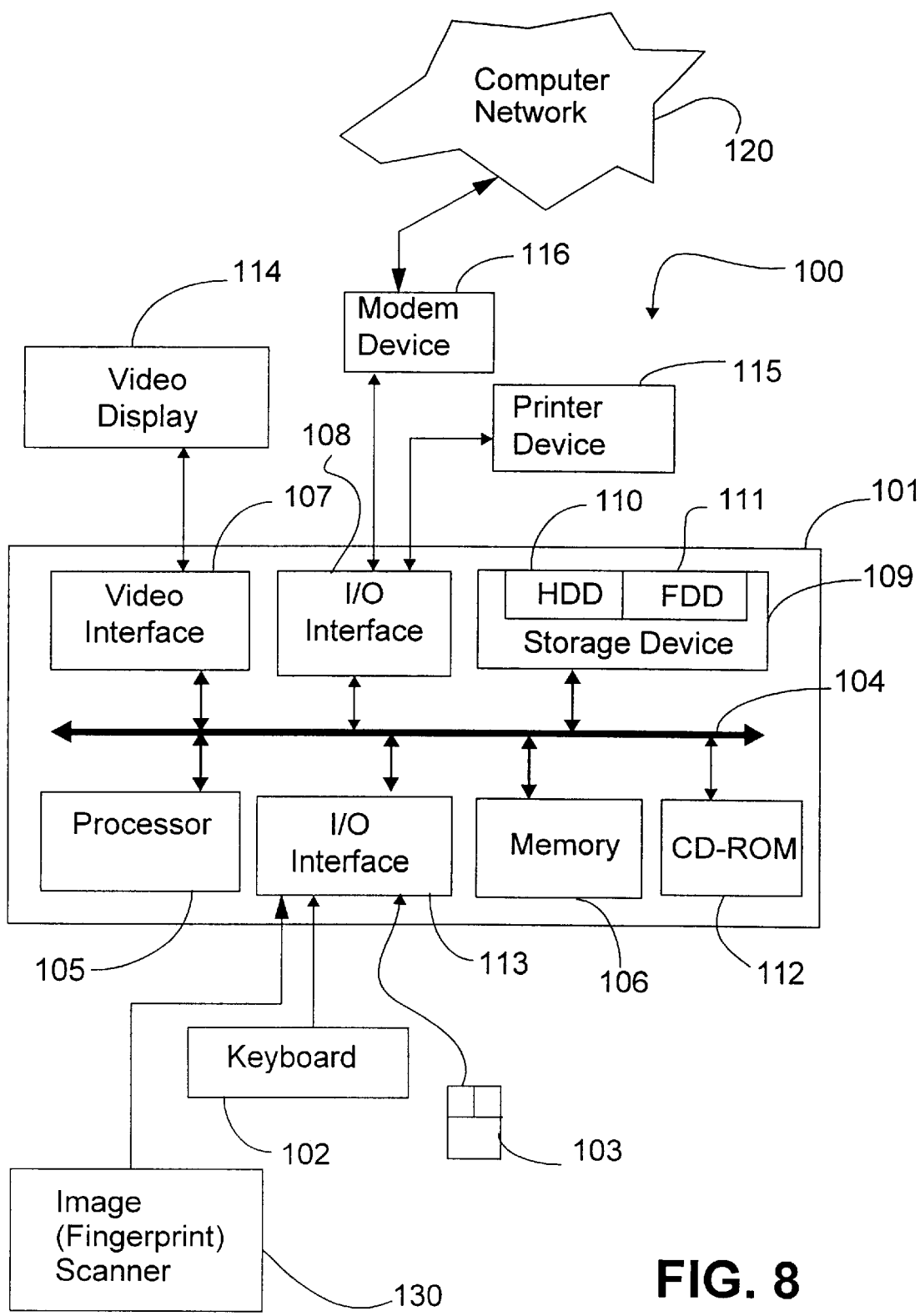
FIG. 8 is a block diagram of a general purpose computer upon which the preferred embodiment of the present invention can be practiced.

As seen in FIG. 8, the computer system includes a scanner 130 connected to the computer module 101 via the I/O interface 113 which may act as a source of image data, such a fingerprint data, for processing by the application program. The scanner 113 may be specifically configured for fingerprint scanning or alternatively may be a general purpose device for hardcopy images. Other sources may typically include the network 120 and data supplied via the CD-ROM drive 112 or the floppy disk drive 111. The database of compressed image data may be formed on the hard disk drive 110 or alternatively/supplementally on the computer network 120. The computer module 101 may also be supplemented by dedicated compression hardware (not illustrated) in those cases where it is not desired for such processing to be handled by the processor 105.

Although the preferred embodiment has been described with reference to fingerprint type images, the inventive principles disclosed herein may be applied to a variety of image types obtained from a variety of sources for a variety of purposes. Such image types are typically characterised by those which display substantial phase uniformity and thus lend themselves to high compression ratios for all image parts excepting where singularities occur. Examples of such images, in addition to fingerprints include synthetic aperture radar images, ultrasonic and sonar images, interferometry images, and images obtained from astronomical, seismic and non-destructive evaluation examinations. Such images essentially form contour maps of phase change and thus exhibit large areas of slow varying phase gradient. This is to be contrasted with images such as real-life bit-maps which display no phase continuity (ie. they exhibit substantial phase noise).

It would be further appreciated by a person skilled in the art that numerous variations and/or modification may be made to the present invention without departing from the spirit or scope of the invention as broadly described. The present embodiment is, therefore, to be considered in all respects to be illustrative and not restrictive.

What is claimed is:

1. A method of encoding a fringe pattern image, said method comprising the steps of:
   demodulating said image to provide a phase map structure of said image;
   identifying and removing any singularities in said phase map structure to create a continuous phase map structure, wherein each of said singularities is removed by adding to said phase map structure a phase spiral of equal charge magnitude and opposite charge sign to said singularity being removed;
   removing $2\pi$ phase discontinuities from said continuous phase map; and
   separately encoding said singularities and said continuous phase map structure as an encoded representation of said image.

2. A method according to claim 1, wherein encoding of said singularities includes encoding at least a position and order of each said singularity.

3. A method according to claim 1, further comprising encoding a significance map of a magnitude of said phase map structure.

4. A method according to claim 3, wherein said continuous phase map structure is separately encoded from significance map.

5. A method according to claim 3, wherein encoding of said continuous phase map structure is performed using said magnitude.

6. A method according to claim 1, wherein said image is of the form:

$$f(x,y)=a(x,y)+b(x,y)\cos(\phi(x,y))+c(x,y)+n(x,y), \phi(x,y)$$

being said phase map structure.

7. A method according to claim 1, wherein said image is selected from the group consisting of a fingerprint image, a synthetic aperture radar image, an ultrasonic image, a sonar image, an interferometry image, an astronomical image, a seismic image, and an image obtained from a non-destructive evaluation procedure.

8. A method of encoding an image, said method comprising the steps of:
(a) providing input data of an image;
(b) demodulating said input data to determine at least a phase mapping structure;
(c) identifying singularities within said phase mapping structure and retaining a separate record of said singularities;
(d) removing said singularities from said phase mapping structure to provide a continuous phase mapping structure;
(e) removing $2\pi$ phase discontinuities from said phase mapping structure;
(f) encoding said continuous phase mapping structure; and
(g) associating said separate record of said singularities with said encoded continuous phase mapping structure to provide an encoded representation of said image.

9. A method according to claim 8, wherein said demodulating further comprises determining an amplitude mapping of said image, and said method comprises the further steps of:
(h) determining a significance mapping based on said amplitude mapping;
(i) encoding said significance mapping; and
(j) associating said encoded amplitude mapping with said separate record and said encoded continuous phase mapping to form part of said encoded representation.

10. A method according to claim 9, wherein step (f) is performed using said significance mapping.

11. A method according to claim 8, wherein each said singularity is represented by a corresponding position, order and orientation.

12. A method according to claim 11, wherein step (d) comprises adding to said phase map structure a phase spiral of equal charge magnitude and opposite charge sign to said singularity being removed.

13. A method according to claim 8, wherein step (f) comprises performing a discrete wavelet transform upon said continuous phase mapping.

14. A method according to claim 9, wherein step (i) comprises performing a discrete wavelet transform upon said significance mapping.

15. A method according to claim 10, wherein step (f) comprises parametrically compressing said continuous phase mapping.

16. A method according to claim 15, wherein said parametrically compressing utilizes one of an n-th order 2-dimensional polynomial (n=1,2,3 . . . ) on a spline fitting arrangement.

17. A method according to claim 8, wherein step (e) precedes steps (c) and (d).

18. A method of handling singularities forming parts of fringe maps, said method comprising the steps of:
demodulating said fringe map to provide a phase mapping structure of said fringe map;
identifying each singularity within said phase mapping structure and forming a corresponding record thereof; and
subtracting each said singularity from said phase mapping structure to form a continuous phase mapping structure, wherein each of said singularities is subtracted by adding to said phase map structure a phase spiral of equal charge magnitude and opposite charge sign to said singularity being subtracted.

19. A method according to claim 18, further comprising associating each said singularity record with a phase value from said continuous phase mapping structure at a location of said singularity record.

20. A method of processing a fringe map, said fringe map including at least one singularity, said method comprising:
performing the method of claim 19; and
processing at least one of:
(a) said corresponding records;
(b) said continuous phase mapping structure; and
(c) said associated records and said phase values.

21. A method of determining a match between an input fringe pattern image and one of a plurality of stored fringe pattern images, each of said images being represented in an encoded form comprising a residual phase mapping and a record of singularities in which each said singularity is associated with a residual phase value of said mapping at a location corresponding to said singularity, said method comprising the steps of:
comparing the record of singularities of said input fringe pattern image with the records of singularities of each said stored fringe pattern image to determine an output group of matching images;
decoding said input fringe pattern image and each image of said output group; and
comparing said input fringe pattern image with each image of said output group to determine a match between said input fringe pattern image and one image of said output group.

22. A method of decoding an encoded representation of an image, wherein said encoded representation comprises at least one phase singularity and encoded amplitude components, said method comprising the steps of:
(a) decoding said encoded representation to provide a phase map structure of said image;
(b) adding said singularities to said phase map structure;
(c) decoding said encoded amplitude components;
(d) combining said amplitude component with said phase map structure; and
(e) inverse transforming said phase map structure to form said image.

23. A method according to claim 22, wherein said phase map structure prior to step (e) is of the form:

$$f(x,y)=a(x,y)+b(x,y)\cos(\phi(x,y)).$$

24. Apparatus for encoding a fringe pattern image, said apparatus comprising:
first means for demodulating said image to provide a phase map structure of said image;

second means for identifying and removing any singularities in said phase map structure to create a continuous phase map structure, wherein each of said singularities is removed by adding to said phase map structure a phase spiral of equal charge magnitude and opposite charge sign to said singularity being removed;

third means for removing 2π phase discontinuities from said continuous phase map; and fourth means for separately encoding said singularities and said continuous phase map structure as an encoded representation of said image.

25. Apparatus according to claim 24, wherein said third means comprises fourth means for encoding said singularities including encoding at least a position and order of each said singularity.

26. Apparatus according to claim 24, further comprising fifth means for encoding a significance map of a magnitude of said phase map structure.

27. Apparatus according to claim 26, wherein said third means comprises sixth means for separately encoding said significance map from said continuous phase map structure.

28. Apparatus according to claim 26, wherein encoding of said continuous phase map structure is performed using said magnitude.

29. Apparatus according to claim 24, wherein said image is of the form:

$$f(x,y)=a(x,y)+b(x,y)\cos(\phi(x,y))+c(x,y)+n(x,y),$$

$\phi(x,y)$ being said phase map structure.

30. Apparatus according to claim 24, wherein said image is selected from the group consisting of a fingerprint image, a synthetic aperture radar image, an ultrasonic image, a sonar image, an interferometry image, an astronomical image, a seismic image, and an image obtained from a non-destructive evaluation procedure.

31. Apparatus for encoding an image, said apparatus comprising:

a demodulator for demodulating said input data to determine at least a phase mapping structure;

means for identifying singularities within said phase mapping structure and retaining a separate record of said singularities;

means for removing said singularities from said phase mapping structure to provide a continuous phase mapping structure;

means for removing 2π phase discontinuities from said phase mapping structure;

means for encoding said continuous phase mapping structure; and means for associating said separate record of said singularities with said encoded continuous phase mapping structure to provide an encoded representation of said image.

32. Apparatus according to claim 31, wherein said demodulator is configured to determine an amplitude mapping of said image, said apparatus further comprising:

means for determining a significance mapping based on said amplitude mapping;

means for encoding said significance mapping; and means for associating said encoded amplitude mapping with said separate record and said encoded continuous phase mapping to form part of said encoded representation.

33. Apparatus according to claim 32, wherein said means for encoding said continuous phase mapping structure utilizes said significance mapping.

34. Apparatus according to claim 31, wherein each said singularity is represented by a corresponding position, order and orientation.

35. Apparatus according to claim 34, wherein said means for removing adds to said phase map structure a phase spiral of equal charge magnitude and opposite charge sign to said singularity being removed.

36. Apparatus according to claim 31, wherein said means for encoding said continuous phase mapping structure performs a discrete wavelet.

37. Apparatus according to claim 32, wherein said means for encoding said significance mapping performs a discrete wavelet transform upon said significance mapping.

38. Apparatus according to claim 33, wherein the encoding of said continuous phase mapping structure comprises parametrically compressing said continuous phase mapping.

39. Apparatus according to claim 38, wherein said parametrically compressing utilizes one of an n-th order 2-dimensional polynomial (n=1,2,3 . . . ) on a spline fitting arrangement.

40. Apparatus for handling singularities forming parts of fringe maps, said apparatus comprising:

means for demodulating said fringe map to provide a phase mapping structure of said fringe map;

means for identifying each singularity within said phase mapping structure and forming a corresponding record thereof; and means for subtracting each said singularity from said phase mapping structure to form a continuous phase mapping structure, wherein each of said singularities is removed by adding to said phase map structure a phase spiral of equal charge magnitude and opposite charge sign to said singularity being subtracting.

41. Apparatus according to claim 40, further comprising means for associating each said singularity record with a phase value from said continuous phase mapping structure at a location of said singularity record.

42. Apparatus for processing a fringe map, said fringe map including at least one singularity, said apparatus comprising:

apparatus according to claim 40; and means for processing at least one of:
 (a) said corresponding records;
 (b) said continuous phase mapping structure; and
 (c) said associated records and said phase values.

43. Apparatus for determining a match between an input fringe pattern image and one of a plurality of stored fringe pattern images, each of said images being represented in an encoded form comprising a residual phase mapping and a record of singularities in which each said singularity is associated with a residual phase value of said mapping at a location corresponding to said singularity, said apparatus comprising:

means for comparing the record of singularities of said input fringe pattern image with the records of singularities of each said stored image to determine an output group of matching images;

means for decoding said input fringe pattern image and each image of said output group; and means for comparing said input fringe pattern image with each image of said output group to determine a match between said input fringe pattern image and one image of said output group.

44. Apparatus for decoding an encoded representation of an image, wherein said encoded representation comprises at least one phase singularity and encoded amplitude components, said apparatus comprising:

means for decoding said encoded representation to provide a phase map structure of said image;

means for adding said singularities to said phase map structure;

means for decoding said encoded amplitude components;

means for combining said amplitude component with said phase map structure; and means for inverse transforming said phase map structure to form said image.

45. A computer readable medium incorporating a computer program product for encoding a fringe pattern image, said computer program product including:

code for demodulating said image to provide a phase map structure of said image;

code for identifying and removing any singularities in said phase map structure to create a continuous phase map structure, wherein each of said singularities is removed by adding to said phase map structure a phase spiral of equal charge magnitude and opposite charge sign to said singularity being removed;

code for removing $2\pi$ phase discontinuities from said continuous phase map; and code for separately encoding said singularities and said continuous phase map structure as an encoded representation of said image.

46. A computer readable medium incorporating a computer program product for handling singularities forming parts of a fringe map, said computer program product including:

code for demodulating said fringe map to provide a phase mapping structure of said fringe map;

code for identifying each singularity within said phase mapping structure and forming a corresponding record thereof; and code for subtracting each said singularity from said phase mapping structure to form a continuous phase mapping structure, wherein each of said singularities is subtracted by adding to said phase map structure a phase spiral of equal charge magnitude and opposite charge sign to said singularity being subtracted.

47. A computer readable medium incorporating a computer program product for decoding an encoded representation of an image, wherein said encoded representation comprises at least one phase singularity and encoded amplitude components, said computer program product including:

code for decoding said encoded representation to provide a phase map structure of said image;

code for adding said singularities to said phase map structure;

code for decoding said encoded amplitude components;

code for combining said amplitude component with said phase map structure; and code for inverse transforming said phase map structure to form said image.

48. An image representation system comprising an encoding arrangement for encoding an image by providing input data of said image;

demodulating said input data to determine at least a phase mapping structure;

identifying singularities within said phase mapping structure and retaining a separate record of said singularities;

removing said singularities from said phase mapping structure to provide a continuous phase mapping structure;

removing $2\pi$ phase discontinuities from said phase mapping structure;

encoding said continuous phase mapping structure; and associating said separate record of said singularities with said encoded continuous phase mapping structure to provide an encoded representation of said image; and a decoding arrangement substantially complementing said encoding arrangement.

49. An image matching system, said system comprising:

(a) a database of compressed image data representing a plurality of images, the compressed image data for each said image including:

(i) a compressed residual phase map obtained by compressing a phase map from which singularities have been removed; and (ii) a record of each said singularity removed from said phase map, said record including a position, order and orientation of each said singularity;

(b) means for extracting from said database for any one said image said record and associating with said position, order and orientation, a value of the local residual phase associated with said singularity;

(c) means for comparing the extracted position, order, orientation and local residual phase of said one image with corresponding values of an input image to determine a match therebetween.

\* \* \* \* \*

UNITED STATES PATENT AND TRADEMARK OFFICE
CERTIFICATE OF CORRECTION

PATENT NO.    : 6,571,014 B1
DATED         : May 27, 2003
INVENTOR(S)   : Kieran Gerard Larkin It is certified that error appears in the above-identified patent and that said Letters Patent is hereby corrected as shown below:

Column 3,
Line 19, "cannot be can be" should read -- cannot be --.

Column 4,
Line 26, "eds" should read -- eds. --; and
Line 63, "Significantly" should read -- Significantly, --.

Column 6,
Line 3, "Consequently" should read -- Consequently, --.

Column 8,
Line 12, "useable or not." should read -- useable. --;
Line 66, "88,90" should read -- 88, 90 --; and
Line 67, "88,90." should read -- 88, 90. --.

Column 9,
Line 1, "88,90," should read -- 88, 90, --;
Line 6, "88,90" should read -- 88, 90 --; and
Line 10, "it's" should read -- its --.

Column 10,
Line 40, "modification" should read -- modifications --.

Column 11,
Line 9, "$\phi(x,y)$" should be deleted; and
Line 10, "being" should read -- $\phi(x,y)$ being --.

UNITED STATES PATENT AND TRADEMARK OFFICE
CERTIFICATE OF CORRECTION

PATENT NO. : 6,571,014 B1
DATED : May 27, 2003
INVENTOR(S) : Kieran Gerard Larkin It is certified that error appears in the above-identified patent and that said Letters Patent is hereby corrected as shown below:

Column 16,
Line 43, "singularity;" should read -- singularity; and --.

Signed and Sealed this

Ninth Day of December, 2003

JAMES E. ROGAN
*Director of the United States Patent and Trademark Office*